United States Patent [19]

Finney

[11] 4,411,261
[45] Oct. 25, 1983

[54] SEMI-RIGID PENILE IMPLANT

[75] Inventor: Roy P. Finney, Tampa, Fla.

[73] Assignee: Medical Engineering Corporation, Racine, Wis.

[21] Appl. No.: 328,827

[22] Filed: Dec. 9, 1981

Related U.S. Application Data

[63] Continuation-in-part of Ser. No. 150,231, May 15, 1980, Pat. No. 4,318,396, and Ser. No. 266,455, May 22, 1981.

[51] Int. Cl.³ .................................................. A61F 5/00
[52] U.S. Cl. ................................................... 128/79
[58] Field of Search .................................. 128/79; 3/1

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,066,073 | 1/1978 | Finney et al. | 128/79 |
| 4,177,805 | 12/1979 | Tudoriu | 128/79 |
| 4,201,202 | 5/1980 | Finney et al. | 128/79 |
| 4,267,829 | 5/1981 | Burton | 128/79 |
| 4,318,396 | 3/1982 | Finney | 128/79 |

Primary Examiner—Dalton L. Truluck
Attorney, Agent, or Firm—Quarles & Brady

[57] ABSTRACT

A penile implant includes a relatively rigid support portion having a stem at one end to be inserted into the root end of a corpus cavernosum of a penis a relatively rigid elongated tip portion with a tip at one end adapted to be implanted in the glans end of the corpus cavernosum, hinge means joining the support portion and tip portion and holding means at the other ends of the support position and tip portion which cooperate to hold the support portion and tip portion of the implant in the form of unitary rigid rod. In a preferred embodiment the holding means at the other ends of the support portion and tip portion are magnets of opposite polarity and the hinge means is a cylindrical sleeve.

5 Claims, 6 Drawing Figures

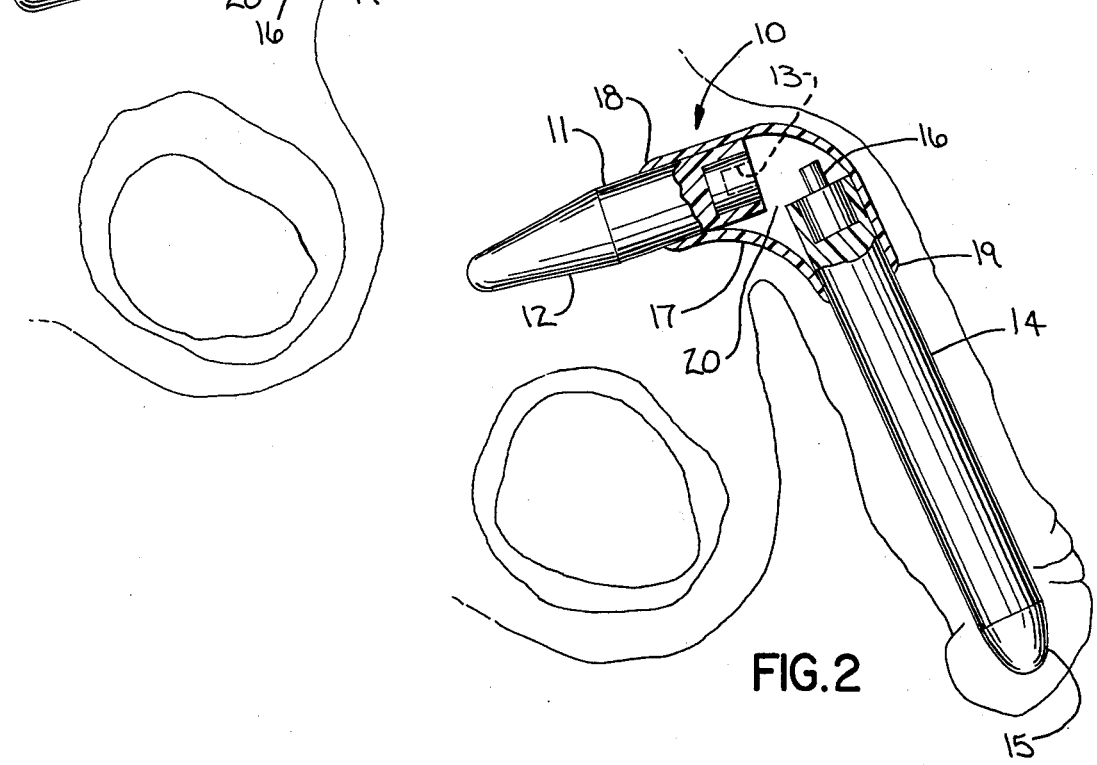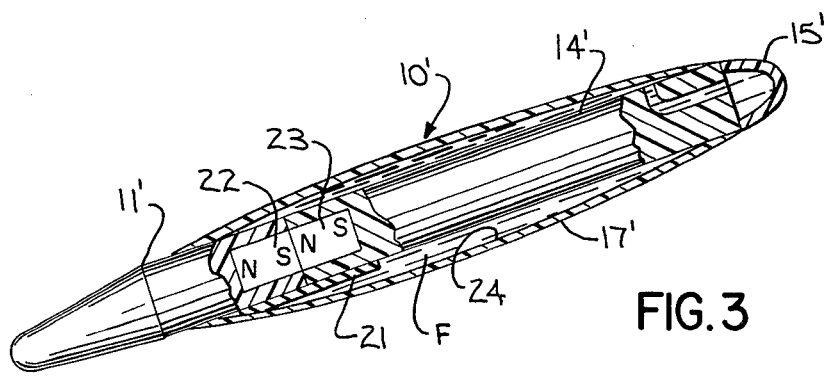

4,411,261

SEMI-RIGID PENILE IMPLANT

RELATED APPLICATIONS

This application is a continuation-in-part of my earlier applications Ser. No. 150,231 filed May 15, 1980 now U.S. Pat. No. 4,318,396 and my copending application Ser. No. 266,455 filed May 22, 1981.

FIELD OF THE INVENTION

The present invention relates to a novel penile implant which can be used in the treatment of erectile impotence. More particularly, it relates to an improved semi-rigid rod penile implant.

BACKGROUND OF THE INVENTION

There are instances of erectile impotence in which the patient does not respond to more conventional therapy, and the surgical implanting of a penile prosthesis is the only practical means of remedying the impotency.

In the past, several types of implantable penile prostheses have been employed. The first and most common type is a pair of identical semi-rigid rods of suitable stiffness. Each of the rods is surgically implanted into a corpus cavernosum of the penis. The implants disclosed in U.S. Pat. Nos. 3,853,122 and 4,066,073 are representative of this type of penile prosthesis.

Another type of penile prosthesis which is available is the inflatable prosthesis. The most common inflatable prosthesis includes a pair of fairly long inflatable and expandable tubes. Each of the tubes is surgically implanted in a corpus cavernosum of the penis. The two tubes are connected by tubing to a pressure bulb of inflating fluid which is implanted elsewhere in the body. Because of the volume required to pressurize, inflate and expand the inflatable tubes, the pressure bulbs are relatively large. For example, in U.S. Pat. No. 3,954,102, an inflatable prosthesis is disclosed in which the fluid is supplied from a single relatively large reservoir which is implanted in the abdominal cavity. The prosthesis of U.S. Pat. No. 4,009,711 includes two implants each having its own relatively large pressurizing bulb which is surgically implanted in the scrotal sac.

The inflatable type implant has an advantage over the semi-rigid rod implant in that its size can be increased to provide a more natural erection. On the other hand, the semi-rigid rod implant is more dependable as the inflatable type can develop leaks.

In U.S. Pat. No. 4,201,202 an implant is disclosed which is a combination semi-rigid rod and inflatable prosthesis. The prosthesis consists of a pair of rods, preferably of the type disclosed in U.S. Pat. No. 4,066,073, which have a flexible sleeve positioned and sealed axially about an intermediate portion of the rod to form a chamber for pressurizing fluid. Each of the implants has a pressure bulb of pressurizing fluid connected by tubing to the chamber so that it can be pressurized and also a valve to depressurize the chamber. A penile erection is achieved by either pressurizing the chambers if a soft rod is used or by manually moving the implants to an erect position if a stiffer hinged rod is used. The implant has an advantage over the conventional semi-rigid rod implant in that the chamber can be pressurized to increase penile girth.

SUMMARY OF THE INVENTION

It is the general object of the present invention to disclose an improved semi-rigid rod penile implant.

The penile implant of the present invention comprises a relatively rigid support portion which has a stem at one end which is intended to be inserted into the root end of a corpus cavernosum of a penis to anchor and support the implant. The implant also includes a relatively rigid elongated tip portion having a tip at one end to be implanted in the portion of the corpus cavernosum in the pendulous penis. The support portion and the tip portion are joined by hinge means and the other ends of the support portion and tip portion are provided with holding means which cooperate to hold the support portion and tip portion of the implant in the form of a unitary rod.

The hinge means is, preferably, a flexible, cylindrical sleeve, which has one end sealed to the support portion and the other end to the tip portion fluid tight manner to provide a chamber for inflating fluid.

In one embodiment the means which cooperate to hold the support portion and the tip portion in the form of a unitary end are magnets of opposite polarity on the other ends of the support portion and tip portion, respectively.

In another embodiment, the other ends of the support and tip portion are provided with innerlocking male and female parts.

BRIEF DESCRIPTION OF THE DRAWINGS

FIG. 1 is a side view, partly in section, showing one embodiment of the penile implant of the present invention implanted in a penis and in an erectile state;

FIG. 2 is a view similar to FIG. 1 showing the implant in a non-erectile state;

FIG. 3 is a side view, in section, of a second embodiment of the implant of the present invention showing the implant in the form it would assume in an erectile state;

DESCRIPTION OF THE PREFERRED EMBODIMENT

Figure 4:
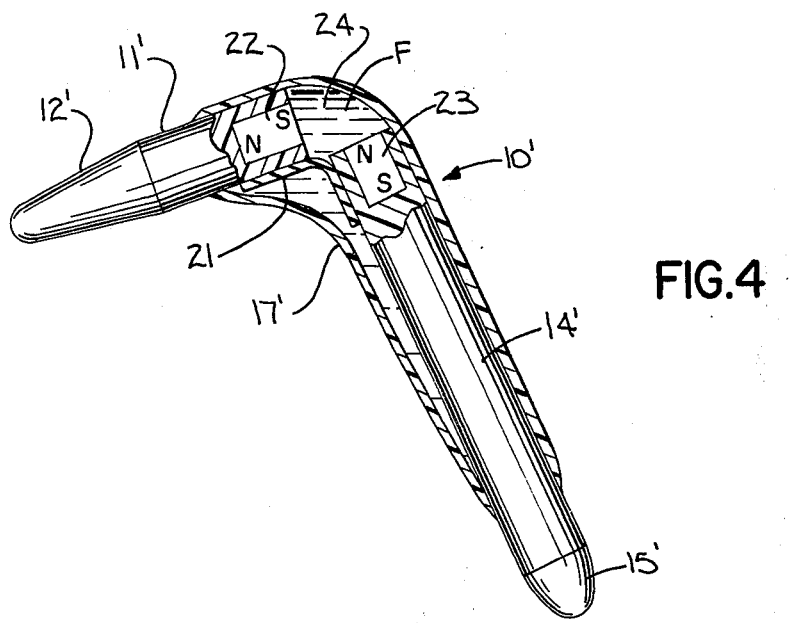
FIG. 4 is a view similar to that of FIG. 3 with the implant of the second embodiment in a non-erectile state.

A penile prosthesis utilizing the implants of the present invention normally will consist of two separate and identical implants each of which is implanted in a separate corpus cavernosum of a penis. However, for purposes of description herein only one implant will be described.

As seen in FIGS. 1 and 2, the penile implant 10 includes a support portion 11 which is constructed of a relatively stiff physiologically inert material such as medical application silicone rubber. At one end the support portion 11 has a short, proximal stem 12 which is to be implanted in the root end of the corpus cavernosum to support and anchor the implant. The other end of the support portion 11 has a female member which is a cylindrical cavity 13. The implant 10 also includes an elongated relatively rigid tip portion 14 which is to be implanted into the portion of the corpus cavernosum in the pendulous penis. The tip portion 14 has a tip 15 at one end which preferably conforms in shape to the inner end of the glans end of the corpus cavernosum of the penis. The other end of the tip portion 14 has a male member in the form of a cylindrical projection 16 which is sized to fit closely in the female member, cavity 13. As seen in FIGS. 1 and 2 the female member, cavity 13, and the male member, projection 16, cooperate to hold the implant 10 in the erectile state seen in FIG. 1.

Still referring to FIGS. 1 and 2 it is seen that a flexible hinge, in the form of a cylindrical sleeve 17 is attached at one end 18 to the support portion 11 and at the other end 19 to the tip portion 15. The ends 18 and 19 are preferably sealed to the walls of the support portion 11 and tip portion 14, respectively, in a fluid-tight manner to form a cylindrical fluid-tight chamber 20. The fluid-tight seals are preferably made with a suitable silicon adhesive although other means of forming a suitable seal may be employed.

Referring still to FIGS. 1 and 2, it can be seen that the flexible hinge, sleeve 17 which connects the support portion 11 to the tip portion 14 allows the tip portion 15 to depend downwardly so that the penis in which the implant 10 is implanted can assume a normal flaccid condition. When the female and male members, cavity 13 and projection 16, respectively, are coupled as seen in FIG. 2, and the support portion 11 and tip portion 14 are united to form a single rigid member. As a result the penis assumes an erectile state, as seen in FIG. 1.

Although in the drawings a single penile implant 10 is shown, as previously described, a complete penile prosthesis will normally include two separate identical penile implants each of which is surgically implanted in a separate corpus cavernosum of the penis.

When properly implanted the stem 12 of the support portion 11 of the implant 10 is positioned in the root end of the corpus cavernosum near the pubic bone to anchor the implant 10, and the paraboloidal tip 15 is positioned in the glans end of the corpus cavernosum. As a result, the implants are positioned correctly in the corpus cavernosum of the penis and the likelihood of displacement is minimized.

In the second embodiment of the invention seen in FIGS. 3 and 4, the implant 10' has a support portion 11' and a tip portion 14' joined by a strap hinge 21. The second embodiment differs from the embodiment of FIGS. 1 and 2, in that the support portion 11' and tip portion 14' do not have male and female members and the sleeve 17' is longer. In place of the male and female members of the first embodiment, the other ends of the support portion 11' and tip portion 14' are provided with magnets 22 and 23, respectively, which are of opposite polarity. The magnets 22 and 23 when brought into proximity cooperate to hold the implant 10' in an erectile position. The longer cylindrical sleeve 17' of the second embodiment preferably is of a material of limited distensibility. It is sealed in a fluid tight manner to the support portion 11 and the tip portion 14' to form a chamber 24 which can be filled with fluid F to increase the girth of the penis in which it is implanted. The chamber 24 is filled by inserting a hollow needle (not shown) through the self sealing tip 15' and adding fluid F until the chamber 24 is expanded to the proper diameter and then withdrawing the needle whereupon the tip 15' reseals.

Figure 5:
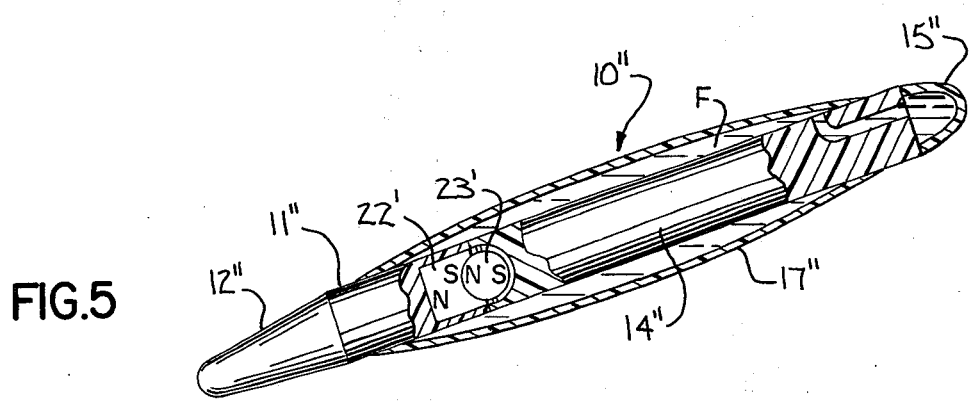
FIG. 5 is a side view similar to that of FIG. 3 showing a third embodiment of the implant of the present invention.
Figure 6:
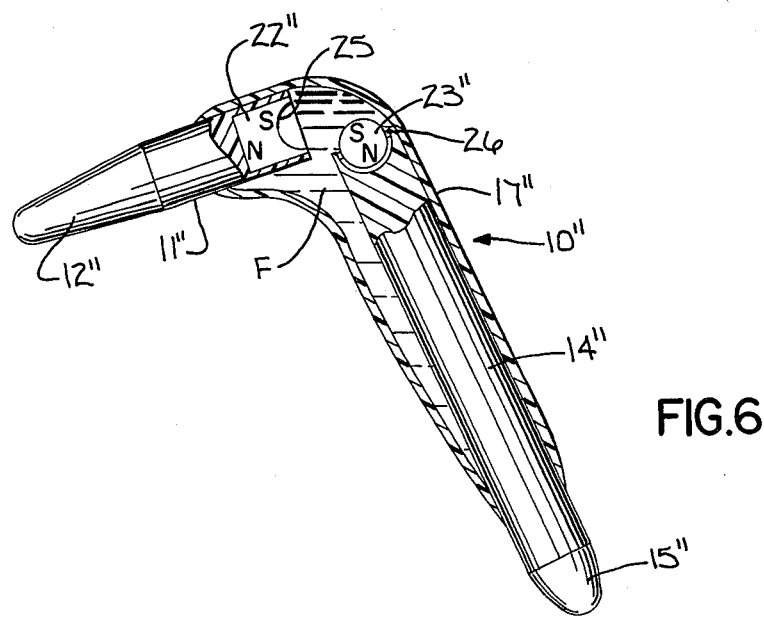
FIG. 6 is a view similar to that of FIG. 5 with the implant of the third embodiment in a non-erectile position.

In the third embodiment of the invention seen in FIGS. 5 and 6 all of components of the implant 10" are identical to that of the second embodiment 10', except that the magnets 22" and 23" are differently shaped. As seen best in FIG. 6 the fixed magnet 22" has a concave recess 25 in its free end and the magnet 23" is a sphere which is supported for rotation upon an axle 26. The magnetic sphere 23" can be manipulated or rotated from outside the penis to present either a N or S pole to the magnet 22". Obviously, if the outer pole of fixed magnet 22" is S and the adjacent pole of the sphere 23" is the opposite pole N, the two magnets will attract and the support portion 11" and tip portion 14" will be joined whereby the penis will assume the erectile position seen in FIG. 5. If, on the other hand, the adjacent poles of the magnets 22" and 23" are of the same polarity, the two magnets will repel and the implant 11" will assume the state seen in FIG. 6.

The configuration of the implant of the present invention obviously may take other forms than those described. However, both the tip portion and support portion should be stiff enough so that when they are united they provide sufficient stability to provide the patient with a usable erection.

In the preferred embodiment of the invention, the support portion of the implant 10 has a Shore hardness of about 70, the tip portion has a Shore hardness of about 20. Preferably the outside of each of the portions is covered with a soft layer of elastomer to minimize tissue trauma. Although materials of the described characteristics are preferred, any material which performs satisfactory under conditions of use can be employed.

The sleeve can be unreinforced elastomer. However, it preferably is of a silicone elastomer coated fabric of limited expansion which is more resistant than an unreinforced elastomer to the wear which can be caused by repeated flexing. The strap hinge is likewise of a tough or reinforced material which can withstand continued flexing.

The preferred method of implantation of the implants is through the perineum. After appropriate incision, the corpus cavernosum is dilated distally and proximally to accept the implant. The appropriate anatomical measurements are made to insure that the stem of the support portion is positioned at the base of the penis below the pelvic bone. An implant having an appropriate girth and length is selected and the tip portion inserted into the glans end of the corpus cavernosum of the penis with the tip positioned in the distal end of the corpus cavernosum. The stem of the support portion may then be trimmed to the desired length and inserted into the root end of the corpus cavernosum. The identical procedure is performed on the other side of the penis and the incision closed to complete the surgical procedure. The stems of the two implants preferably diverge laterally to accommodate the anatomy and provide lateral stability to the penis.

It will be readily apparent to those skilled in the art that a variety of changes and modifications might be made without departing from the spirit and scope of the invention. For example, the other ends of the support portion and the tip portion, if desired, may be provided with both interlocking male and female members and magnets of opposed polarity to provide additional holding strength. Furthermore, the sleeve of the first embodiment may be longer and form a fluid tight chamber which can be filled to increase the girth of the penis. Therefore, the scope of the invention is not to be limited except by the claims which follow:

I claim:

1. In a penile implant comprising a relatively rigid support portion having a stem at one end for insertion into the root end of a corpus cavernosum of a penis; a separate relatively rigid, elongated tip portion with a tip at one end for insertion in the glans end of the corpus cavernosum and an intermediate portion comprising a flexible sleeve connected at one end to the support portion and at the other end to the tip portion, the improvement which comprises providing said other ends of the support portion and tip portion with attachment means which can be used to removably attach the support portion and tip portion together in the form of a unitary rod.

2. The implant of claim 1 in which the attachment means is a pair of magnets of opposed polarity on the other ends of the support portion and the tip portion, respectively.

3. The implant of claim 1 in which the attachment means are mating female and male elements on the other ends of the tip portion and support portion.

4. The implant of claim 1 in which the flexible sleeve cooperates with the support and tip portions to form a fluid tight chamber which can be inflated with fluid to increase the girth of the implant.

5. The implant of claim 1 in which the sleeve is made of a material of limited expansion.

* * * * *